(12) United States Patent
Wheeler et al.

(10) Patent No.: US 7,041,091 B2
(45) Date of Patent: May 9, 2006

(54) PACKAGING SYSTEM AND METHOD FOR PERSONAL CARE ABSORBENT ARTICLES

(75) Inventors: Katherine C. Wheeler, Menasha, WI (US); Kenneth R. Casson, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 171 days.

(21) Appl. No.: 10/732,169

(22) Filed: Dec. 10, 2003

(65) Prior Publication Data

US 2005/0131376 A1 Jun. 16, 2005

(51) Int. Cl.
*A61F 13/15* (2006.01)
*A61F 13/20* (2006.01)

(52) U.S. Cl. .................. 604/391; 604/385.03

(58) Field of Classification Search ........... 604/358, 604/391, 385.03, 385.05; 206/225
See application file for complete search history.

(56) References Cited

U.S. PATENT DOCUMENTS

| | | | | |
|---|---|---|---|---|
| 4,505,704 | A | * | 3/1985 | Roeder .................. 604/385.05 |
| 4,598,528 | A | * | 7/1986 | McFarland et al. ........... 53/430 |
| 4,692,162 | A | * | 9/1987 | Binker et al. .......... 604/385.13 |
| 4,770,298 | A | | 9/1988 | McFarland et al. |
| 4,772,282 | A | | 9/1988 | Oakley |
| 4,775,310 | A | | 10/1988 | Fischer |
| 4,776,068 | A | | 10/1988 | Smirlock et al. |
| 5,071,414 | A | * | 12/1991 | Elliott .................. 604/385.13 |
| 5,300,058 | A | * | 4/1994 | Goulait et al. .............. 604/391 |
| 5,358,499 | A | * | 10/1994 | Seidy .................. 604/385.03 |
| 5,392,498 | A | | 2/1995 | Goulait et al. |
| 5,565,255 | A | | 10/1996 | Young et al. |
| 5,611,790 | A | | 3/1997 | Osborn, III et al. |
| 5,618,583 | A | | 4/1997 | Young et al. |
| 5,676,652 | A | | 10/1997 | Hunter et al. |
| 5,778,457 | A | * | 7/1998 | Conway .................. 2/406 |
| 5,876,531 | A | | 3/1999 | Jacobs et al. |
| 5,964,741 | A | | 10/1999 | Moder et al. |
| 5,986,165 | A | * | 11/1999 | Moder et al. .............. 604/358 |
| 5,988,386 | A | * | 11/1999 | Morrow .................. 206/581 |
| 6,013,062 | A | | 1/2000 | Dilnik |
| 6,077,255 | A | | 6/2000 | Hunter et al. |
| 6,136,405 | A | | 10/2000 | Young et al. |
| 6,163,939 | A | | 12/2000 | Lacey et al. |

(Continued)

FOREIGN PATENT DOCUMENTS

DE 7923932 8/1979

(Continued)

OTHER PUBLICATIONS

U.S. Appl. No. 10/732,907, filed Dec. 10, 2003.

(Continued)

*Primary Examiner*—Tatyana Zalukaeva
*Assistant Examiner*—Paula L. Craig
(74) *Attorney, Agent, or Firm*—Dority & Manning (57) ABSTRACT

An absorbent article, such as a feminine care product, includes a liquid permeable top cover, a generally liquid impermeable baffle, and an absorbent structure disposed between the top cover and outer cover. The garment facing side of the baffle includes hook material as a primary attachment mechanism between the baffle and the undergarment. The top cover is a hook compatible material that is releasably attachable to the hook material such that the article can be rolled into a tube-like configuration wherein the hook material is releasably engaged with the hook compatible material for maintaining the article in a rolled configuration.

24 Claims, 4 Drawing Sheets

U.S. PATENT DOCUMENTS

| | | | |
|---|---|---|---|
| 6,254,582 B1 * | 7/2001 | O'Donnell et al. | 604/385.05 |
| 6,312,417 B1 | 11/2001 | Hansson | |
| 6,484,371 B1 | 11/2002 | Romanko et al. | |
| 6,582,411 B1 | 6/2003 | Carstens et al. | |
| 2003/0065302 A1 * | 4/2003 | Kuroda et al. | 604/385.13 |
| 2004/0102748 A1 * | 5/2004 | Hirotsu | 604/358 |

FOREIGN PATENT DOCUMENTS

| | | |
|---|---|---|
| EP | 0699427 | 3/1996 |
| EP | 0699427 A1 * | 3/1996 |
| EP | 0752239 A1 | 1/1997 |
| EP | 0699427 B1 | 6/1999 |
| EP | 0752239 B1 | 4/2000 |
| EP | 1245209 A2 | 10/2002 |
| EP | 1300125 A2 | 4/2003 |
| WO | 9507677 | 3/1995 |
| WO | 9918022 | 4/1999 |
| WO | 9930659 | 6/1999 |
| WO | 0037002 | 6/2000 |
| WO | WO 01/72254 A2 * | 3/2001 |
| WO | 0147457 A1 | 7/2001 |
| WO | 0167911 A2 | 9/2001 |
| WO | 0172254 A2 | 10/2001 |
| WO | 0172254 A3 | 10/2001 |

OTHER PUBLICATIONS

U.S. Appl. No. 10/742,605, filed Dec. 19, 2003.
International Search Report, filed Mar. 29, 2005.
Written Opinion, filed Mar. 29, 2005.

* cited by examiner

PACKAGING SYSTEM AND METHOD FOR PERSONAL CARE ABSORBENT ARTICLES

FIELD OF THE INVENTION

The present invention relates generally to the field of disposable absorbent articles, and more particularly to a method for packaging feminine care articles.

BACKGROUND

Disposable absorbent articles intended to be worn in the crotch portion of an undergarment are well known. The basic form of such absorbent articles typically includes a bodyside liquid-permeable cover, a garment-side liquid-impermeable baffle, and an absorbent core positioned between the cover and the baffle. Such absorbent articles are now in wide use as sanitary napkins, panty shields, panty liners, and adult incontinence pads. While this invention is directed to all such products, for purposes of simplification, the invention will be described with reference to a sanitary napkin.

Present day commercial products have generally performed well, remaining in place and providing the user with ease of placement and removal. Such products typically use an adhesive strip applied to the garment facing side of the baffle for attachment of the article to the wearer's undergarment. The adhesive strip is covered with a peel strip that is removed by the wearer prior to placing the article in the crotch region of the undergarment. These products are typically folded, for example in a tri-fold configuration, and packaged in individual disposable pouches or the like. A number of the pouches are, in turn, packaged in cartons, soft-side packages, and so forth, which are eventually purchased by the consumer. In other commercial embodiments, the peel strip is omitted and the article is attached directly to the pouch or other wrapper material, wherein the combination is then folded into an individual pouch or package. For use, the wearer opens the pouch, peels the article from the pouch material and places the article in the undergarment. Regardless of the method, the process of packaging the individual articles adds significantly to the overall cost and materials of the articles.

Additionally, the use of adhesives for attaching the articles can present certain drawbacks. For example, the inner crotch surface of an undergarment, to which these products are typically adhered, is continually being distorted, twisted and stretched during use due to the dynamics of the wearer. As a result, conventional adhesive attachments can detach causing the undesirable consequence of the sanitary napkin moving out of place. Further, while the sanitary napkin may frequently reattach itself, due to the continuing adhesive nature of the pressure sensitive adhesive, reattachment often places the sanitary napkin in an undesirable position wherein the sanitary napkin does not function properly. Additionally, once the adhesive has been exposed and the article placed into the crotch region of the undergarment, it is generally not practical to remove and reposition the article. In an extreme case, the attachment of the adhesive also results in the adhesive folding over on itself and then becoming unavailable for reattachment.

The industry is continually seeking ways to improve feminine care absorbent articles and, in this light, articles offering an improved attachment mechanism that compliments a more beneficial and economic packaging process would be desirable.

SUMMARY

Objects and advantages of the invention will be set forth in part in the following description, or may be obvious from the description, or may be learned through practice of the invention.

Although the present invention has particular usefulness in the field of feminine care articles such as panty shields or liners and sanitary napkins, it should be appreciated that any manner of personal care absorbent article may benefit from the invention, including incontinence articles, and the like. All such uses are within the scope and spirit of the invention. For ease of description only, the working environment of the invention is assumed to be feminine care sanitary napkins.

The invention relates to a unique absorbent article configuration that allows the article to be rolled into a compact and discrete tube-like configuration prior to use. The article includes conventional features such as a generally liquid permeable top cover, a generally liquid impermeable and vapor permeable outer cover or baffle, and an absorbent structure disposed between the top cover and baffle. The opposite sides of the article releasably engage with each other and, thus, the article is easily rolled and maintained in its rolled configuration without the need for additional retaining means, such as adhesives, ties, tabs, or the like. For use, a wearer simply unrolls the article and attaches the baffle side of the article directly to the undergarment without the use of adhesives.

Articles according to the invention also provide a means to discretely dispose of soiled articles without the need for disposal wrappers, pouches, or the like. After removing the article from the undergarment, the wearer can simply grasp the edges of the article and roll the product up with the baffle side outwardly facing. The soiled top cover is thus not visible and the article will hold its rolled configuration without additional adhesives or the like for subsequent disposal.

In a particular embodiment, the article is rolled from one longitudinal end thereof towards an opposite longitudinal end. In an alternate embodiment, the article is rolled from one lateral side thereof towards an opposite lateral side. The article may be rolled such that the baffle side is outwardly facing. This may be desired to protect and keep the top cover sanitary.

Once rolled, the articles may be directly packaged in any conventional packaging materials. Alternatively, the rolled articles may be individually wrapped with conventional wrapping materials prior to being packaged.

The top cover is formed of a hook compatible material, such as a nonwoven material. The article utilizes unique placement of hook-type attachment material in a pattern on the garment facing side of the baffle for the purposes of attaching the baffle directly to the undergarment without additional attachment devices, and for holding the article in its rolled tube-like configuration by releasably engaging with the cover sheet material.

The pattern of hook material defined on the baffle may be any desired continuous or discontinuous placement pattern, for example stripes, dashes, swirls, dots or island-like regions, etc. The amount and pattern of the hook material should be sufficient to ensure that the baffle remains secured in the crotch region of the undergarment yet does not render the baffle substantially vapor impermeable. In a desirable embodiment, the garment facing side of the baffle presents an overall uniform pattern of hook material generally over its entire surface area such that a uniform vapor permeability profile is established. For example, the hook material may be provided in generally longitudinally disposed deposits such that a vapor permeability profile of a transverse section of the article at one longitudinal end is generally the same for a comparable transverse section in the medial or opposite longitudinal end of the article.

The garment will thus be retained in the undergarment more securely than if a single area or region of conventional adhesive were used, such as a longitudinal strip of adhesive along the center of the baffle as with many types of commercial articles. Yet, even with such improved attachment, the article is remains breathable and is easily removable and variably positionable as required by the wearer.

In a particular embodiment, the pattern may be defined by stripes of the hook material having a width of about one-half of a distance between adjacent stripes. The stripes may be, for example, about one-eight inch and spaced apart about one-fourth inch. The regions of hook material in the patterns may be between about 5% to about 75% of a total surface area of the garment facing side of the baffle. In a particular embodiment, the hook material may be between about 25% to about 50% of the total surface area such that at least about 50% of the baffle remains breathable.

The degree of engagement of the hook material with the top cover should not result in appreciable damage to the top cover material. There is a desirable range of engagement that may be empirically determined depending on the shape and type of the hooks, type of cover material, shape of the absorbent article, and so forth. Peel values of less than 500 grams-force are generally desired. Engagement with peel values between about 50 grams-force to about 100 grams-force should result in little or no damage to conventional nonwoven cover sheet materials.

The hook material may be deposited on the baffle by conventional methods, including by applying strips of hook material tape with adhesive, etc. In a particularly desirable embodiment, the hook material is extruded and laminated directly onto a base material used for the baffle, as described in greater detail below.

If desired, an additional absorbent device, such as a tampon or interlabial device, may be placed in the article and rolled therewith such that the article is essentially wrapped around the additional device. In this way, the wearer is presented with two devices (if needed) in a single compact rolled configuration.

The invention also encompasses absorbent articles as described herein that are capable of being rolled and packaged in such rolled configuration.

Additionally, the invention encompasses a method for rolling uniquely formed absorbent articles into a compact tube-like configuration for packaging.

Aspects of the invention will described below in greater detail by reference to particular embodiments, examples of which are illustrated in the figures.

DETAILED DESCRIPTION

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Referring to the Figures, in which like numerals indicate like parts throughout the several views, embodiments of a disposable absorbent article 10 are depicted. For purposes of illustration only, the disposable absorbent article 10 is exemplified as a sanitary napkin. Typically, a sanitary napkin is worn by a female to absorb body fluids, such as menses, blood, urine and other body excrements discharged during a menstrual period. Although the invention has particular usefulness for feminine care articles and, it should be appreciated that the invention is in no way limited to sanitary napkins in particular, or to feminine care articles in general. One skilled in the art will readily understand the adaptability of the invention to other personal care and health care articles, such as, for example, panty liners, adult incontinence garments and the like that attach to a wearer's undergarment.

The term "disposable", as used herein, means that the absorbent article is discarded after a single use and is not intended to be laundered for subsequent reuse.

Referring to the figures in general, the absorbent article 10 according to the invention includes a generally liquid permeable top cover 12, a generally liquid impermeable and vapor permeable outer cover or baffle 14, and an absorbent structure 20 disposed between the top cover 12 and baffle 14. The top cover 12 and baffle 14 are sealed together at their peripheral edges utilizing known techniques, such as, for example, gluing, crimping, hot-sealing or the like, the sealed edges defining an overall sealed peripheral edge 15. The article 10 may take on various shapes, but will generally have opposite longitudinal ends A, B and lateral sides C, D. In the illustrated embodiments, the article 10 has a well-known hourglass shape. Various other geometries of absorbent articles, including feminine care articles, are well known to those skilled in the art, and all such embodiments are within the scope and spirit of the invention.

The absorbent article 10 is desirably provided with sufficient capacity to absorb and retain the intended amount and type of bodily exudate(s). The absorbent capacity is provided by the fluid retentive absorbent structure or web 20. The absorbent structure 20 can be any structure or combination of components which are generally compressible, conformable, non-irritating to a wearer's skin, and capable of absorbing and retaining liquids and certain body wastes. For example, the structure 20 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material is a matrix of cellulosic fluff, and may also include superabsorbent hydrogel-forming particles. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

The absorbent structure 20 can contain superabsorbent materials which are effective in retaining body fluids. As a general rule, the superabsorbent material is present in the absorbent web in an amount of from about 0 to about 90 weight percent based on total weight of the web. Superabsorbents have the ability to absorb a large amount of fluid in relation to their own weight. Typical Superabsorbents used in absorbent articles, such as sanitary napkins, can absorb anywhere from 5 to 60 times their weight in body fluids. Superabsorbent materials are well known in the art and can be selected from natural, synthetic, and modified natural polymers and materials.

The absorbent web material may also be a coform material. The term "coform material" generally refers to composite materials comprising a mixture or stabilized matrix of thermoplastic fibers and a second non-thermoplastic material. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The absorbent web material utilized in the absorbent structure 20 is also selected so that the individual absorbent structure possesses a particular individual total absorbency depending on the intended article of use. For example, for infant care products, the total absorbency can be within the range of about 200–900 grams of 0.9 wt % saline, and can typically be about 500 g of saline. For adult care products, the total absorbency can be within the range of about 400–2000 grams of saline, and can typically be about 1300 g of saline. For feminine care products, the total absorbency can be within the range of about 7–50 grams of menstrual fluid, and can typically be within the range of about 30–40 g of menstrual fluid.

The absorbent structure 20 may be a multi-component and may include, for example, an intake layer or transfer delay layer in combination with the underlying absorbent web. Such configurations are well known to those skilled in the art.

The fluid permeable top cover 12 has an outwardly facing surface that may contact the body of the wearer and receive bodily exudate(s). The top cover 12 desirably is made of a material which is flexible and non-irritating to the wearer. As used herein, the term "flexible" is intended to refer to materials which are compliant and readily conform to the bodily surface(s) with which such materials are in contact, or materials which respond by easily deforming in the presence of external forces.

The top cover 12 is provided for comfort and conformability and functions to direct bodily exudate(s) away from the body, through the top cover 12 and toward the absorbent structure 20. The top cover 12 should retain little or no liquid in its structure so that the cover provides a relatively comfortable and non-irritating surface next to the tissues within the vestibule of a female wearer. The top cover 12 can be constructed of any woven or nonwoven material which is easily penetrated by bodily fluids which contact the surface of the cover. Examples of suitable cover materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. The cover may be apertured to increase its fluid intake capacity. A specific example of a suitable cover material is a bonded carded web made of polypropylene and polyethylene such as that used as cover stock for KOTEX® pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable cover 12 can also contain a plurality of apertures formed therein which are intended to increase the rate at which bodily fluid(s) can penetrate through the cover and into the absorbent structure 20.

The top cover 12 may also be embossed with any desired embossing pattern to define embossed channels. Embossing techniques are well known to those skilled in the art. An embossing pattern not only creates an aesthetically pleasing surface, the channels facilitate intake of menses fluid. Menses will tend to flow along the densified edges of the channels rather than pool on contact points of the top cover 12.

The top cover 12 can be maintained in secured relation with the absorbent structure 20 by bonding all or a portion of the adjacent surfaces to one another. A variety of bonding methods known to one of skill in the art can be utilized to achieve any such secured relationship. Examples of such methods include, but are not limited to, the application of adhesives in a variety of patterns between the two adjoining surfaces, entangling at least portions of the adjacent surface of the absorbent with portions of the adjacent surface of the cover, or fusing (thermal, ultrasonics, etc.) at least portions of the adjacent surface of the cover to portions of the adjacent surface of the absorbent.

The baffle 14 has an outer garment facing side 16 and may be any one of a number of suitable liquid impermeable materials known in the art for use as outer covers or baffles in absorbent articles. Preferably, the baffle 14 will permit the passage of air and moisture vapor out of the article 10 while blocking the passage of body fluids. A suitable material is a micro-embossed polymeric film, such as polyethylene or polypropylene, having a thickness of about 0.025 to 0.13 millimeters. Bicomponent films can also be used, as well as woven and nonwoven fabrics which have been treated to render them liquid impermeable. A specific example of a baffle material is a polyethylene film such as that used in KOTEX® pantiliners and obtainable from Pliant Corporation, Schaumburg, Ill., USA. The cover can be maintained in secured relation with the absorbent structure 20 by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces.

Although not illustrated in the figures, it should be understood that the article 10 may include laterally extending wings that aid in securing the article 10 to the wearer's undergarment. Such wings are well known in the art and generally function by folding around the edges of the undergarment crotch region and attaching to each other.

A hook material 22 is provided in a pattern on the garment facing side 16 of the baffle 14. The hook material 22 is defined in the pattern desirably over substantially the entire surface of the garment facing side 16. The particular design, shape, etc., of the pattern are not limiting features. The pattern should provide sufficient coverage of hook material 22 to ensure reliable attachment of the article 10 to the wearer's undergarment. Undergarments are typically made from various woven or non-woven materials that present an attachment surface for conventional hook materials. Thus, the hook material 22 on the garment facing side 16 of the baffle 14 may attach directly to the inner or body facing side of wearer's undergarment, and can provide the primary attachment mechanism between the article 10 and the garment.

The amount of the hook material 22 relative to the entire surface area of the body facing side 16 may vary between about 5% to about 75%, with desirable coverage being about 10% to about 50% of the surface area. In a particular embodiment, the coverage is about 25%. Desirably, the amount of coverage of the hook material 22 should be such that at least about 50% of the baffle 14 is not covered by hook material and remains vapor permeable.

As mentioned, the pattern of the hook material 22 may vary, but is desirably defined by deposits of hook material 22 interspaced with "bare" regions 18 of the baffle material 14. The pattern may include generally longitudinally disposed deposits such that the vapor permeability profile of the baffle 14 is generally uniform over the surface area of the baffle 14 in that the permeability of a random transverse section of the article is generally uniform over the length of the article. However, generally horizontal deposits of the hook material 22 are within the scope and spirit of the invention. In a particular embodiment illustrated in FIGS. 1 through 4, the hook material is defined in a pattern of continuous longitudinal stripes 28 having a width of, for example, about one-eight of an inch. The stripes 28 are interspaced with bands 30 of bare baffle material having a width of, for example, one-quarter of an inch. Thus, the surface area of the hook material 22 is about one-half of that of the bare baffle regions 30 of baffle material.

In an alternate embodiment, the pattern of hook material 22 may be defined in different complementary patterns. For example, in the embodiment of FIG. 6, the hook material 22 is defined in a pattern of discontinuous deposits, such as the illustrated pattern of broken stripes or alternating "dashes-." The discontinuous deposits may be, for example, island-like deposits such as circles, dots, etc., or deposits of irregular shapes. It should be appreciated that any desired pattern or shape of hook material deposits are within the scope and spirit of the invention.

The hook material 22 essentially constitutes the male component of conventional hook-and-loop mechanical fastening systems and cooperates with a "loop" or loop-like material to define a releasable and re-attachable fastening system. Any number of commercially available and conventional micro-hook materials used in absorbent articles, including diaper attachment tabs, etc., may be used in the present invention. Conventional systems are, for example, available under the VELCRO® trademark. The hook element may be provided by a single-prong hook configuration, a multiple-prong hook configuration or by a generally continuous, expanded-head configuration, such as provided by a mushroom-head type of hook element. The many arrangements and variations of such fastener systems are collectively known in the art as hook-and-loop fasteners.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 which corresponds to U.S. Pat. No. 5,624,429 which issued Apr. 29, 1997, the entire disclosure of which is hereby incorporated by reference in a manner which is consistent herewith.

In a particularly desirable embodiment of the invention, the hook material 22 is directly extruded onto the baffle material 14 to define laminated regions of the hook material 22 integral with the baffle material 14. Processes for directly extruding regions of a hook material directly onto a base material are described, for example, in U.S. Pat. Nos. 5,518,795; 5,260,015; and 5,744,080, all from Velcro Industries B.V. and incorporated herein in their entirety for all purposes. The extrusion process described in these patents may be used to directly deposit or embed the hook material 22 with the baffle material 14 in any desired pattern. The baffle material 14 is selected so as to be suitable for the extrusion process and to support the embedded hook material 22. From a manufacturing perspective, rolls of the baffle material 14 having the hook material already embedded therein may be supplied directly into an in-line processing line for producing the articles 10. The extruded embedded regions of hook material 22 also have a reduced thickness as compared to the hooked regions of conventional hook tape adhered to a base material.

The top cover 12 is made of a material 32 that is "hook compatible" with the hook material 22 on the baffle 14 and, thus, is releasably attachable to the baffle 14 when the article 10 is rolled in accordance with the invention. "Hook-compatible" material 32 should be understood to encompass any material functioning as a loop or loop-like surface for releasable attachment with the hook material 22. Suitable materials include, for example, a woven fabric, a nonwoven fabric, a knitted fabric, a perforated or apertured layer, and the like, as well as combinations thereof. Any number and combination of suitable cover materials may provide the "hook compatible" feature.

As seen, for example, in FIGS. 2, 4, 6, and 7, the unique configuration of the article 10 according to the invention allows the article to be rolled into a compact and discrete tube-like configuration prior to use. Because the top cover 12 and baffle 14 are releasably attachable, as described above, the article 10 is easily rolled and maintained in its rolled configuration without the need for additional retaining means, such as adhesives, ties, tabs, or the like. For use, the wearer simply unrolls the article 10 and attaches the baffle 14 directly to their undergarment by way of the hook material 22 provided on the garment facing side 16 of the baffle 14.

Figure 6:
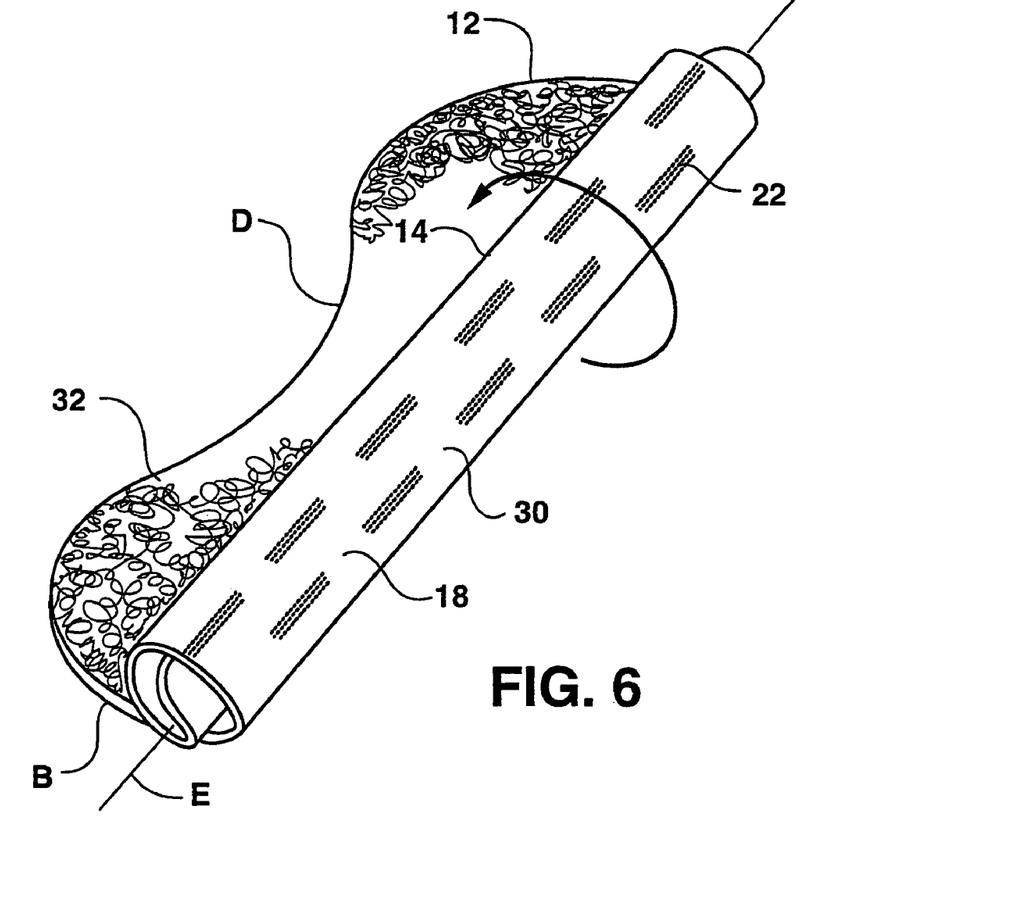
FIG. 6 is a perspective view of an alternate embodiment of an article according to the invention being rolled from one lateral side thereof to the opposite lateral side.

It should be appreciated that the articles 10 can be rolled in various ways. For example, referring to FIG. 2, the article 10 is rolled from longitudinal end A towards the opposite longitudinal end B such that the resulting rolled configuration has a roll axis E. Alternatively, as illustrated in FIG. 6, the article 10 may be rolled from a lateral side C towards the opposite lateral side D such that the resulting rolled article 10 has a longitudinally extending roll axis E.

Figure 1:
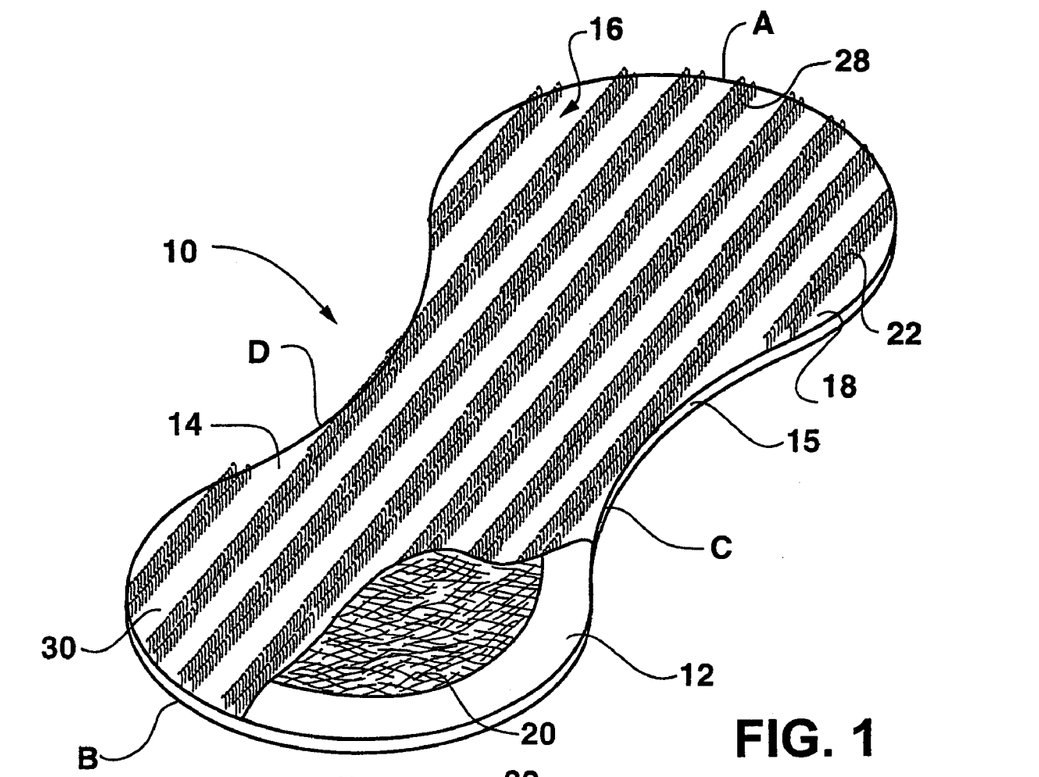
FIG. 1 is a perspective partial cut-away view of an absorbent article according to the invention.
Figure 2:
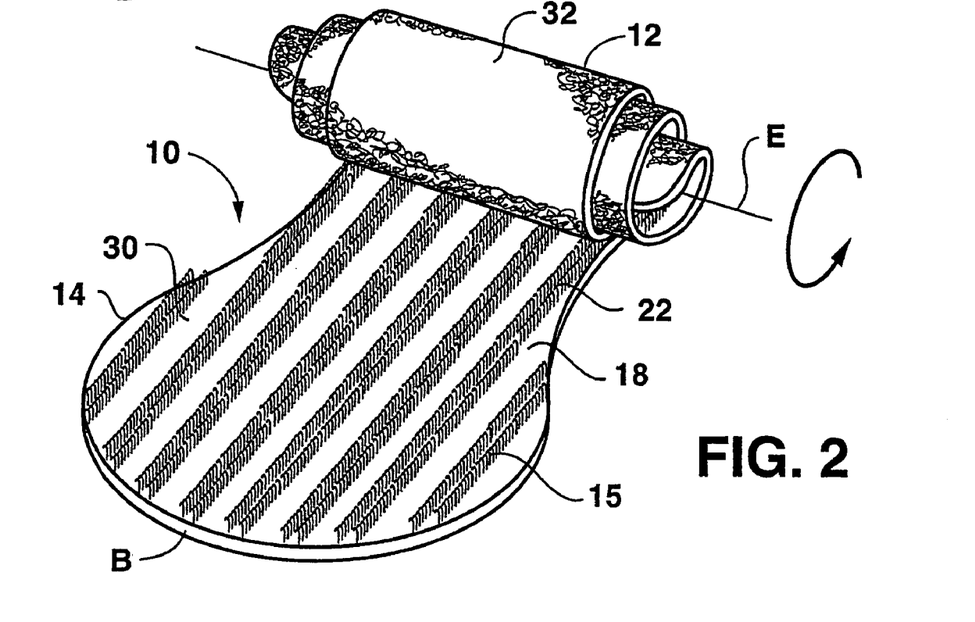
FIG. 2 is a perspective view of the absorbent article according to FIG. 1 being rolled from one longitudinal end towards the opposite longitudinal end.
Figure 3:
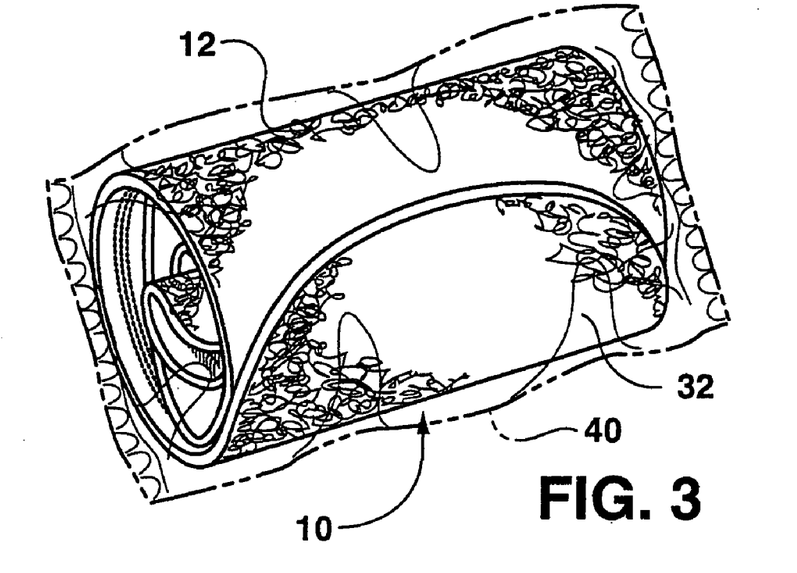
FIG. 3 is a perspective view of an absorbent article according to the invention in a rolled and wrapped configuration.
Figure 4:
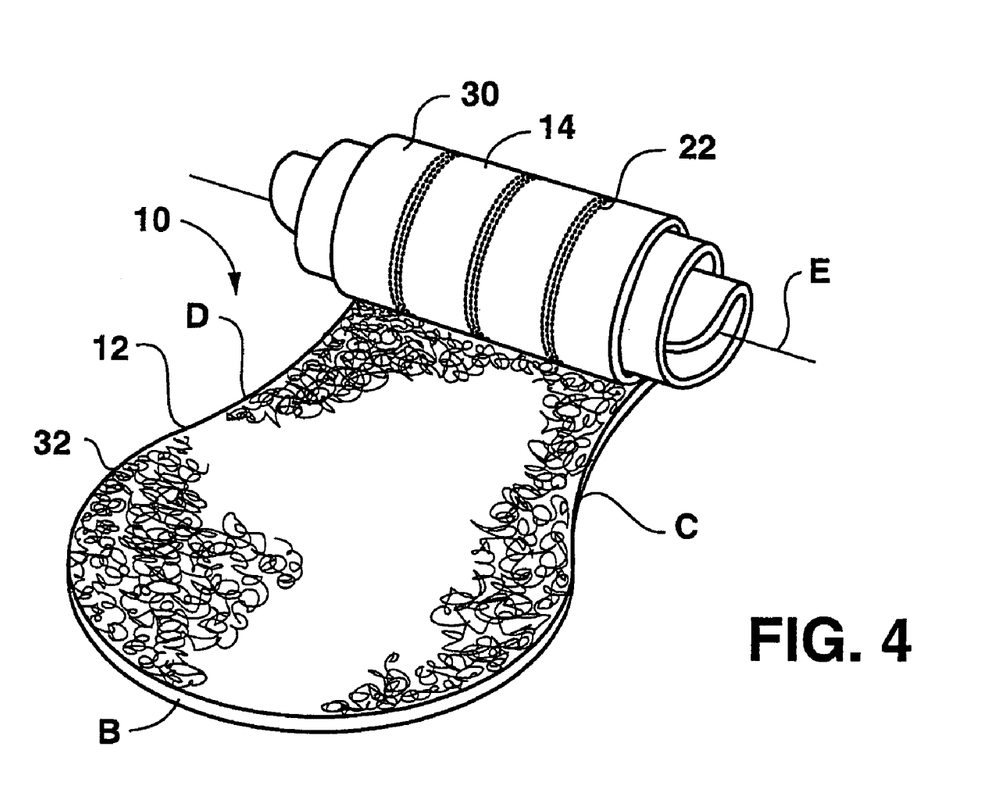
FIG. 4 is a perspective view of an article being rolled in a direction opposite to that of FIG. 2 such that the top cover is outwardly facing.

The articles 10 may be rolled such that the top cover 12 is outwardly facing, as in FIGS. 2 and 3. In an alternate embodiment, the articles 10 may be rolled such that the baffle 14 is outwardly facing, such as in FIGS. 4 through 6. This orientation may be desirable to protect and keep the top cover 12 clean.

The degree of engagement of the hook material 22 with the top cover 12 should not result in appreciable damage to the top cover material. There is a desirable range of engagement that may be empirically determined depending on the shape and type of the hooks, type of cover material, shape of the absorbent article, and so forth. Peel values of less than 500 g are generally desired. Engagement with peel values between about 50 g to about 100 g should result in little or no damage to conventional nonwoven cover sheet materials.

Figure 7:
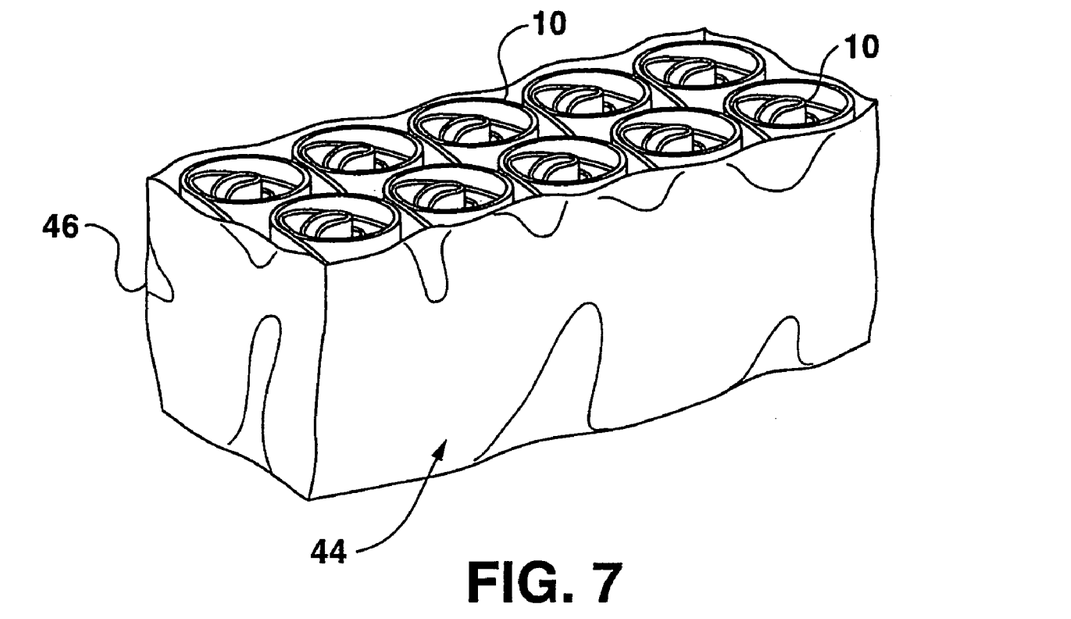
FIG. 7 is a perspective view of packaged rolled articles according to the invention.

Once rolled, the articles 10 may be packaged in various ways. As illustrated in FIG. 7, the articles 10 may be packaged directly with any conventional soft-side (i.e., plastic or film) or rigid (i.e., paperboard) packaging material 46 to form a package 44 of rolled articles 10. The articles 10 may be oriented in any desired manner in the package 44.

Figure 5:
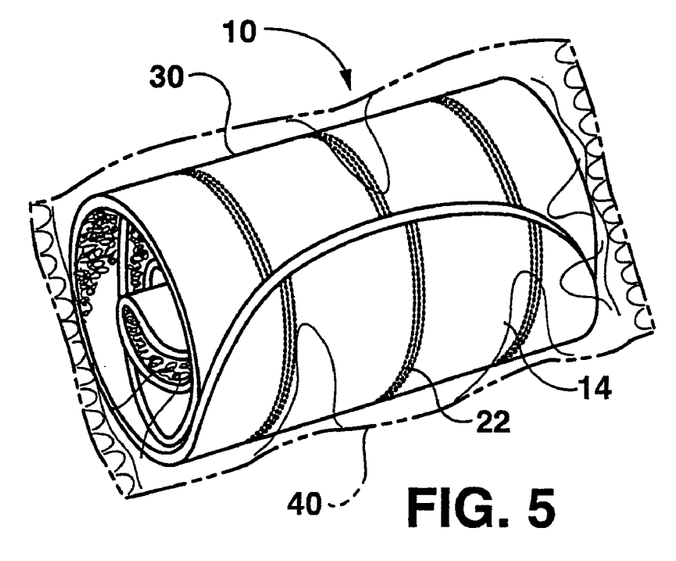
FIG. 5 is a perspective view of the absorbent article of FIG. 4 in a rolled and wrapped configuration.

In may also be desired to individually wrap the articles 10 with any conventional wrapping material 40, as illustrated in FIGS. 3 and 5 prior to packaging the articles. The individual wrapper may also be used by the consumer to dispose of soiled articles.

Articles 10 according to the invention also provide a means to discretely dispose of soiled articles without the need for disposal wrappers, pouches, or the like. After removing the article 10 from the undergarment, the wearer can simply grasp the edges of the article 10 and roll it such that the baffle 14 is outwardly facing. The soiled top cover 12 is thus not visible and the article will hold this rolled configuration without additional adhesives or the like for subsequent disposal.

Figure 8:
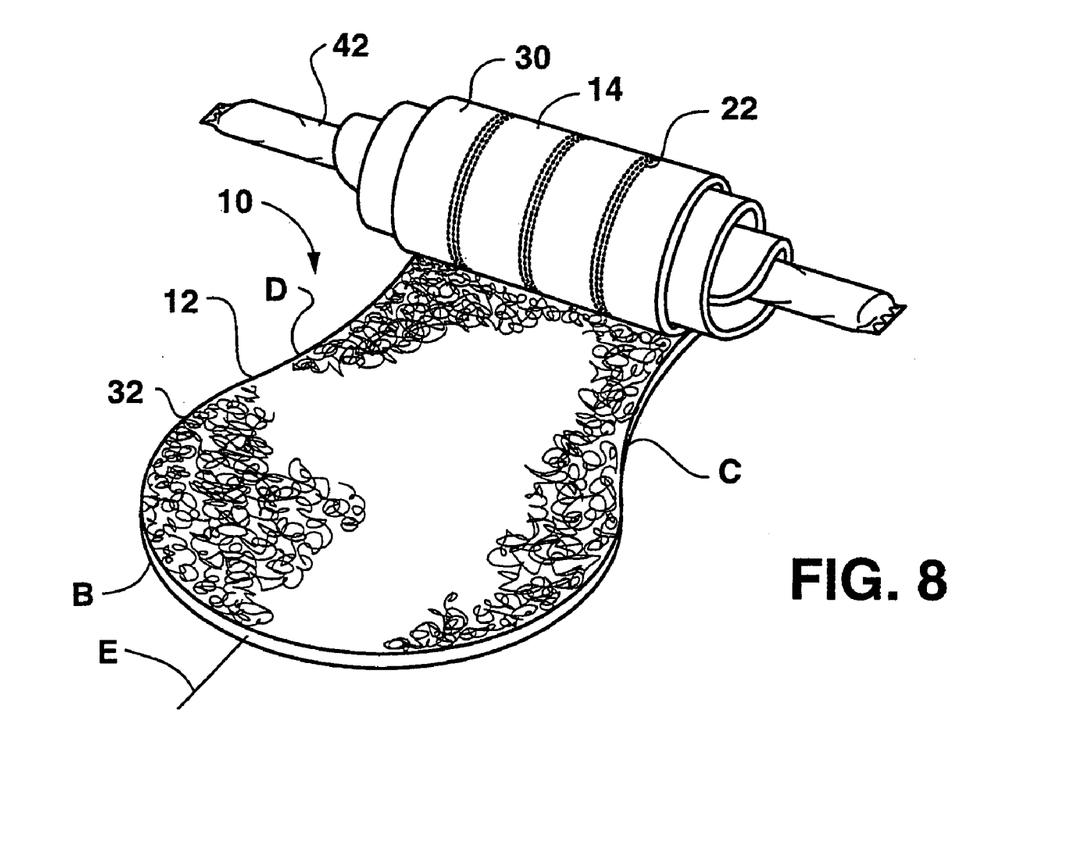
FIG. 8 is a perspective view of an article according to the invention being rolled with an additional absorbent device.

Referring to FIG. 8, the rolled tube-like configuration also provides a convenient and efficient means to include an additional personal care device 42, such as any conventional vaginal insert device, including tampons, interlabial devices, and so forth, with each article 10. Thus a protection system of two articles is provided to the consumer is a discrete and compact package. The additional device 42 may be separately wrapped so that if the device is not needed, the consumer may simply store it for later use.

It should be appreciated by those skilled in the art that various modifications and variations can be made to the embodiments of the absorbent article described herein without departing from the scope and spirit of the invention as set forth in the appended claims and equivalents thereof.

What is claimed is:

1. A rolled absorbent article for placement in the crotch region of an undergarment, comprising:

a generally liquid permeable top cover;

a generally liquid impermeable baffle having a garment facing side;

an absorbent structure disposed between said top cover and said baffle;

said garment facing side of said baffle comprising hook material defined in a pattern on the surface thereof, said hook material providing a primary attachment mechanism between said baffle and the undergarment;

said top cover comprising a hook compatible material that is releasably attachable to said hook material on said garment facing side of said baffle; and said article rolled into a tube-like configuration wherein said hook material is releasably engaged with said hook compatible material for maintaining said article in said rolled configuration.

2. The absorbent article as in claim 1, wherein said article is rolled from one longitudinal end thereof towards an opposite longitudinal end.

3. The absorbent article as in claim 1, wherein said article is rolled from one lateral side thereof towards an opposite lateral side.

4. The absorbent article as in claim 1, wherein said article is wrapped in a wrapping material.

5. The absorbent article as in claim 1, wherein said article is rolled such that said baffle is outwardly facing.

6. The absorbent article as in claim 1, wherein said pattern of hook material comprises longitudinally disposed stripes of said hook material.

7. The absorbent article as in claim 6, wherein said stripes of said hook material have a width of about one-half of a distance between adjacent said stripes.

8. The absorbent article as in claim 1, wherein said hook material is defined on between about 5% to about 75% of a total surface area of said garment facing side of said baffle in an amount and placed to ensure that said hook material securely attaches said article to a wearer's undergarment.

9. The absorbent article as in claim 8, wherein said baffle comprises a generally uniform vapor permeability profile over the surface area thereof.

10. The absorbent article as in claim 9, wherein said hook material is defined in a pattern of spaced longitudinal stripes.

11. The absorbent article as in claim 8, wherein said hook material is defined in generally continuous regions extending from one lateral side or longitudinal end of said article to an opposite respective lateral side or longitudinal end.

12. The absorbent article as in claim 8, wherein said hook material is defined in generally discontinuous regions.

13. The absorbent article as in claim 1, wherein said hook compatible material of said top cover comprises a liquid permeable nonwoven material.

14. The absorbent article as in claim 1, wherein said baffle comprises a base material with said hook material deposited thereon.

15. The absorbent article as in claim 14, wherein said hook material is formed and laminated directly onto said base material.

16. The absorbent article as in claim 1, wherein said article is one of a sanitary napkin, panty liner, and adult incontinent article.

17. The absorbent article as in claim 1, further comprising an additional personal care absorbent device rolled into said article.

18. The absorbent article as in claim 17, wherein said additional personal care absorbent device comprises a vaginal insert device.

19. An absorbent article for placement in the crotch region of an undergarment, comprising:

a generally liquid permeable top cover;

a generally liquid impermeable and vapor permeable baffle having a garment facing side;

an absorbent structure disposed between said top cover and said baffle;

said garment facing side of said baffle comprising a base material and a hook material laminated directly onto said base material in a pattern such that said hook material provides a sole attachment mechanism between said baffle and the undergarment;

said top cover comprising a hook compatible material that is releasably attachable to said hook material on said garment facing side of said baffle and wherein said hook material is defined on said baffle in a pattern of spaced apart regions such that transverse medial and longitudinal end sections of the article have generally the same vapor permeability profiles.

20. The absorbent article as in claim 19, wherein said hook material is disposed on said baffle in a pattern such that said baffle comprises a generally uniform vapor permeability profile over the surface area thereof.

21. The absorbent article as in claim 20, wherein said pattern of hook material comprises longitudinally disposed stripes of said hook material.

22. The absorbent article as in claim 21, wherein said stripes of said hook material have a width of about one-half of a distance between adjacent said stripes.

23. The absorbent article as in claim 20, wherein said hook material is defined on about 25% of a total surface area of said garment facing side of said baffle.

24. The absorbent article as in claim 19, wherein said hook material is defined in generally discontinuous regions.

* * * * *